US010295534B2

(12) United States Patent
Kashiwagi et al.

(10) Patent No.: US 10,295,534 B2
(45) Date of Patent: May 21, 2019

(54) METHOD FOR MEASURING ANTI-DRUG ANTIBODY

(71) Applicant: JIMRO Co., Ltd., Takasaki (JP)

(72) Inventors: Nobuhito Kashiwagi, Takasaki (JP); Fumio Saitoh, Takasaki (JP); Kenta Kaneda, Takasaki (JP); Hidetaka Maegawa, Takasaki (JP); Yuko Yagihashi, Takasaki (JP)

(73) Assignee: JIMRO CO., LTD., Takasaki-shi (JP)

( * ) Notice: Subject to any disclaimer, the term of this patent is extended or adjusted under 35 U.S.C. 154(b) by 0 days.

(21) Appl. No.: 15/498,930

(22) Filed: Apr. 27, 2017

(65) Prior Publication Data

US 2017/0315118 A1 Nov. 2, 2017

Related U.S. Application Data

(63) Continuation of application No. PCT/JP2016/082135, filed on Oct. 28, 2016.

(30) Foreign Application Priority Data

Apr. 27, 2016 (JP) ................. 2016-089301

(51) Int. Cl.
| | |
|---|---|
| G01N 31/00 | (2006.01) |
| G01N 33/53 | (2006.01) |
| G01N 33/564 | (2006.01) |
| G01N 33/68 | (2006.01) |
| G01N 33/94 | (2006.01) |

(52) U.S. Cl.
CPC ....... *G01N 33/564* (2013.01); *G01N 33/6854* (2013.01); *G01N 33/94* (2013.01); *G01N 2333/4716* (2013.01)

(58) Field of Classification Search
CPC combination set(s) only.
See application file for complete search history.

(56) References Cited

U.S. PATENT DOCUMENTS

| | | |
|---|---|---|
| 9,140,701 B2 | 9/2015 | Robinson et al. |
| 2015/0226758 A1 | 8/2015 | Grabert et al. |

FOREIGN PATENT DOCUMENTS

| | | |
|---|---|---|
| JP | 1-224666 | 9/1989 |
| JP | 2012-510618 | 5/2012 |
| WO | WO 2010/065425 A1 | 6/2010 |
| WO | WO 2015/123315 A1 | 8/2015 |

OTHER PUBLICATIONS

Yoshinoya et al. (Journal of Clinical Laboratory Immunology, 1992, vol. 38, pp. 161-173) Abstract Only.*
Wang et al. (Journal of Immunological Methods, vol. 382, 2012, pp. 177-188).*
Sethu etal. (Clinical Immunology, 2013, vol. 148, pp. 177-185).*
Biorad—ADA ELISA protocol dated Mar. 10, 2015.*
Sethu (Clinical Immunology, 2013, vol. 148, pp. 177-185).*
International Search Report dated Jan. 24, 2017 in PCT/JP2016/082135 filed on Oct. 28, 2016 (with English translation).

Written Opinion dated Jan. 24, 2017 in PCT/JP2016/082135 filed on Oct. 28, 2016 (with English translation).
A. Vultaggio, et al., "Anti-infliximab IgE and non-IgE antibodies and induction of infusion-related severe anaphylactic reactions", Allergy, 2010, vol. 65, 5 pgs.
Kazuo Watanabe et al., "Detection of immune complexes by monoclonal anti-Cl q and anti-C3d ELISA systems", Jpn. J. Clin, Immun, 1989, 12 pgs, (with partial English translation).
Uri Kopylov, et al., "Clinical Utility of Antihuman Lambda Chain-based Enzyme-linked Immunosorbent Assay (ELISA) Versus Double Antigen ELISA for the Detection of Anti-infliximab Antibodies", Inflammatory bowel diseases, vol. 18, (9), 2012, 6 pgs.
Sadayoshi Yoshinoya, et al., "Circulating Immune Complex Levels Measured by New ELISA Kits Utilizing Monoclonal Anti-C1q and Anti-C3d Antibodies Correlate with Clinical Activities of SLE but not with those of RA", Journal of clinical and laboratory immunology, vol. 38, (4), 1992, 13 pgs.
Nicole Casadevall, et al., "Pure Red-Cell Aplasia and Antierythropoietin Antibodies in Patients Treated with Recombinant Erythropoietin", The New England Journal of Medicine, vol. 346, (7), 2002, 7 pgs.
Matthew P. Baker, et al., "Immunogenicity of protein therapeutics", Self/Nonself, vol. 1, Issue 4, 2010, 9 pgs.
Shui-Long Wang, et al., "Development and validation of a homogeneous mobility shift assay for the measurement of infliximab and antibodies-to-infliximab levels in patient serum", Journal of Immunological Methods, 2012, 12 pgs.
Extended European Search Report dated Oct. 24, 2017 in Patent Application No. 17167959.0.
Swaminathan Sethu, et al. "Immunoglobulin 01 and immunoglobulin 04 antibodies in multiple sclerosis patients treated with IFNβ interact with the endogenous cytokine and activate complement", Clinical Immunology, vol. 148, No. 2, XP028674566, 2013, pp. 177-185.
Urs E. Nydegger, et al "Circulating Immune Complexes in the Serum in Systemic Lupus Erythematosus and in Carriers of Hepatitis B antigen", The Journal of Clinical Investigation, vol. 54, No. 2. XP002363777. 1974. pp. 297-309.
Eric K Mibei, et al. "CR1 Binding Assay: A Novel Elisa Assay for Measuring Circulating Immune Complexes", European Scientific Journal, vol. 10, No. 33 , XP055414356, 2014, pp. 125-137.
R. Baur, et al. "Relevance of a circulating immune complex assay (CIC) to distinguish between patients with autoimmune thyroid diseases and healthy controls (ELISA, C1q, Anti-C1q, IgM, IgG)". Journal of Steroid Biochemistry, vol. 20, No. 6, XP023421132, 1984, p. 1638.
Tsue-Ming Lin, et al. "An Enzyme-Linked Immunoassay for Circulating Immune Complexes Using Solid Phased Goat C1q", Journal of Immunological Methods, vol. 63, No. 2, XP024351404, 1983, pp. 187-205.
C T K A Da Costa, et al. "Anti-C3d neoantigen-based immune complex ELISA assays for diagnostic and immunopathogenetic investigation of HIV-associated tuberculosis", Serodiagnosis and Immunotherapy in Infectious Disease, vol. 6, No. 3, XP026462369, 1994, pp. 108-112.
Montserrat Carrasco-Triguero, et al. "Application of a Plug-and-Play Immunogenicity Assay in Cynomolgus Monkey Serum for ADCs at Early Stages of Drug Development," Journal of Immunology Research, vol. 2016, XP055415092, 2016, pp. 1-14.
R. D'Amelio, et al. "Antigen-specific detection of soluble immune complexes in conglutinin-binding assays", Clin. Exp. Immunol, vol. 45, XP055414439, 1981, pp. 283-289.

\* cited by examiner

*Primary Examiner* — Lisa V Cook

(74) *Attorney, Agent, or Firm* — Oblon, McClelland, Maier & Neustadt, L.L.P.

(57) ABSTRACT

Provided is a method for measuring anti-drug antibodies ADAs appearing in a patient receiving molecular-targeted therapy in a simpler and more accurate manner.

9 Claims, 6 Drawing Sheets

[FIG. 1-A]

Division of Biological Chemistry and Biologicals, National Institute of Health Sciences, April 1, 2016

| Classification | Name | Trade Name | Structure | Target | Main indications | Year of approval US / EU / Japan | Producing cell |
|---|---|---|---|---|---|---|---|
| Mouse antibody | | | | | | | |
| | muromonab-CD3 | Orthoclone OKT3 | IgG2a | CD3 | acute rejection after kidney transplantation | 1986 / NA / 1991 | mouse hybridoma |
| | ibritumomab tiuxetan | Zevalin | IgG1κ (MX-DTPA; 90Y-labeled) | CD20 | B-cell non-Hodgkin's lymphoma | 2002 / 2004 / 2008 | CHO |
| | | Zevalin | IgG1κ (MX-DTPA; 111In-labeled) | | Confirmation of accumulation site for ibritumomab tiuxetan | / / 2008 | CHO |
| | iodine 131 Tositumomab | Bexxar | IgG2aλ [131I-labeled] | CD20 | non-Hodgkin's lymphoma | 2003 / NA / NA | mammalian cell |
| | catumaxomab | Removab | mIgG2a×(EpCAM), rhIgG2bλ(CD3; EpCAM, CD3 | | cancerous ascites | NA / 2009 / NA | rat/mouse hybridoma |
| | blinatumomab | Blincyto | scFv-scFv | CD19, CD3 | acute lymphocytic leukemia | 2014 / 2015 / NA | CHO |
| Chimeric antibody | | | | | | | |
| | abciximab | ReoPro | IgG1 (Fab) | GPIIb/IIIa | myocardial ischemia | 1994 / NA / NA | mammalian cell |
| | rituximab | Rituxan/MabThera | IgG1κ | CD20 | B-cell non-Hodgkin's lymphoma | 1997 / 1998 / 2001 | CHO |
| | basiliximab | Simulect | IgG1κ | CD25 | acute rejection after kidney transplantation | 1998 / 1998 / 2002 | Sp 2/0 |
| | infliximab | Remicade | IgG1κ | TNFα | rheumatoid arthritis | 1998 / 1999 / 2002 | Sp 2/0 |
| | cetuximab | Erbitux | IgG1κ | EGFR | head and neck cancer, colorectal cancer | 2004 / 2004 / 2008 | Sp 2/0 |
| | brentuximab vedotin | Adcetris | IgG1 (MMAE-modified) | CD30 | Hodgkin's lymphoma | 2011 / 2012 / 2014 | CHO |
| | siltuximab | Sylvant | IgG1κ | IL-6 | Castleman's disease | 2014 / 2014 / NA | CHO |
| | dinutuximab | Unituxin | IgG1κ | GD2 | neuroblastoma (children) | 2015 / 2015 / NA | Sp 2/0 |
| | obiltoxaximab | Anthim | IgG1κ | B. anthracis tc | inhalational anthrax | 2016 / NA / NA | |
| Humanized antibody | | | | | | | |
| | daclizumab | Zenapax | IgG1κ | CD25 | acute rejection after kidney transplantation | 1997 / 1999 / NA | NS0 |
| | palivizumab | Synagis | IgG1κ | RSV F protein | RS virus infection | 1998 / 1999 / 2002 | NS0 |
| | trastuzumab | Herceptin | IgG1κ | HER2 | metastatic breast cancer | 1998 / 2000 / 2001 | CHO |
| | gemtuzumab ozogamicin | Mylotarg | IgG4κ (calicheamicin-modified) | CD33 | acute myeloid leukemia | 2000 refused / 2005 | NS0 |
| | alemtuzumab | Campath | IgG1κ | CD52 | B-cell chronic lymphocytic leukemia | 2001 / 2001 / 2014 | CHO |
| | omalizumab | Xolair | IgG1κ | IgE | asthma | 2003 / 2005 / 2009 | CHO |
| | efalizumab | Raptiva | IgG1κ | CD11 | psoriasis vulgaris | 2003 / 2004 / NA | CHO |
| | bevacizumab | Avastin | IgG1κ | VEGF | colorectal cancer | 2004 / 2005 / 2007 | CHO |
| | natalizumab | Tysabri | IgG4κ | α4Integrin | multiple sclerosis | 2004 / 2006 / 2014 | murine myeloma cell |
| | tocilizumab | Actemra | IgG1κ | IL-6R | Castleman's disease, rheumatoid arthritis | 2010 / 2009 / 2005 | CHO |
| | ranibizumab | Lucentis | IgG1κFab | VEGF-A | age-related macular degeneration | 2006 / 2007 / 2009 | E.Coli |
| | eculizumab | Soliris | IgG2/4κ | C5 | paroxysmal nocturnal hemoglobinuria | 2007 / 2007 / 2010 | NS0 |
| | certolizumab pegol | Cimzia | Fab'+PEG | TNFα | rheumatoid arthritis, severe Crohn's disease | 2008 / 2009 / 2012 | E.Coli |
| | mogamulizumab | Potelligeo | IgG1κ | CCR4 | CCR4-positive adult T-cell leukemia lymphoma | NA / NA / 2012 | CHO |
| | pertuzumab | Perjeta | IgG1κ | HER2 | HER2-positive inoperable or recurrent breast cancer | 2012 / 2013 / 2013 | CHO |
| | trastuzumab emtansine | Kadcyla | IgG1κ (maytansine-modified) | HER2 | HER2-positive metastatic recurrent breast cancer | 2013 / 2013 / 2013 | CHO |
| | obinutuzumab | Gazyva | IgG1 | CD20 | chronic lymphocytic leukemia | 2013 / 2014 / NA | CHO |
| | vedolizumab | Entyvio | IgG1 | α4β7 Integrin | Crohn's disease | 2014 / 2014 / NA | CHO |
| | pembrolizumab | Keytruda | IgG4κ | PD-1 | melanoma | 2014 / 2015 / NA | CHO |
| | idarucizumab | Praxbind | IgG1 Fab | dabigatran | neutralization of dabigatran (Pradaxa(R)) | 2015 / 2015 / NA | CHO |
| | mepolizumab | Nucala | IgG1κ | IL-5 | asthma | 2015 / 2015 / NA | CHO |
| | elotuzumab | Empliciti | IgG1κ | SLAMF7 | multiple myeloma | 2015 / 2016 / NA | NS0 |
| | daratumumab | Darzalex | IgG1κ | CD38 | multiple myeloma | 2015 / NA / NA | CHO |
| | ixekizumab | Taltz | IgG4 | IL-17A | psoriasis vulgaris | 2016 / NA / NA | CHO |
| | reslizumab | Cinqair | IgG4κ | IL-5 | asthma | 2016 / NA / NA | NS0 |
| Human antibody | | | | | | | |
| | adalimumab | Humira | IgG1κ | TNFα | rheumatoid arthritis | 2002 / 2003 / 2008 | CHO |
| | panitumumab | Vectibix | IgG2κ | EGFR | colorectal cancer | 2006 / 2007 / 2010 | CHO |
| | golimumab | Simponi | IgG1κ | TNFα | rheumatoid arthritis | 2009 / 2009 / 2011 | Sp 2/0-Ag14 |
| | ustekinumab | Stelara | IgG1κ | IL-12, IL-23-p40 | psoriasis | 2009 / 2009 / 2011 | Sp 2/0-Ag14 |
| | canakinumab | Ilaris | IgG1κ | IL-1β | cryopyrin-associated periodic syndrome | 2009 / 2009 / 2011 | NS0 |
| | ofatumumab | Arzerra | IgG1κ | CD20 | chronic lymphocytic leukemia | 2009 / 2010 / 2013 | NS0 |
| | denosumab | Prolia/Xgeva Ranmark | IgG2 | RANKL | bone lesion, osteoporosis | 2010 / 2010 / 2012 | CHO |
| | ipilimumab | Yervoy | IgG1 | CTLA4 | melanoma | 2011 / 2011 / 2015 | CHO |
| | belimumab | Benlysta | IgG1λ | BlyS | SLE | 2011 / 2011 / NA | NS0 |
| | raxibacumab | | IgG1λ | B. anthracis tc | inhalational anthrax, pulmonary anthrax | 2012 / NA / NA | murine cell |
| | ramucirumab | Cyramza | IgG1 | VEGFR2 | gastric cancer | 2014 / 2014 / 2015 | NS0 |
| | nivolumab | Opdivo | IgG4 | PD-1 | malignant melanoma | 2014 / 2015 / 2014 | CHO |
| | secukinumab | Cosentyx | G1/κ | IL-17—A | psoriasis vulgaris, arthropathic psoriasis | 2015 / 2015 / 2014 | CHO |
| | evolocumab | Repatha | IgG2 | PCSK9 | hypercholesterolemia | 2015 / 2015 / 2015 | CHO |
| | alirocumab | Praluent | IgG1 | PCSK9 | hypercholesterolemia | 2015 / 2015 / NA | CHO |
| | necitumumab | Portrazza | IgG1κ | EGFR | non-small cell lung cancer | 2015 / 2015 / NA | NS0 |

NA: Not approved

[FIG. 1-B]

| Biologic name | Company | Type | Target | Indication(s) | Reported Immunogenicity |
|---|---|---|---|---|---|
| Prolastin | Talecris biotherapeutics | PD | α1-proteinase inhibitor | α1-antitrypsin deficiency | None reported |
| Aralast | Baxter Healthcare | PD | α1-proteinase inhibitor | α1-antitrypsin deficiency | None reported |
| Zemaira | Aventis Behring (CSL Behring) | PD | α1-proteinase inhibitor | α1-antitrypsin deficiency | None reported |
| Kogenate FS | Bayer (Bayer Schering Pharma) | rHu | Factor VIII | Hemophilia A | 15% |
| ReFacto | Genetics Institute (Wyeth) | rHu | Factor VIII | Hemophilia A | 30% |
| Zyntha | Wyeth (Pfizer) | rHu | Factor VIII | Hemophilia A | 2.2% (89) |
| NovoSeven | NovoNordisk | rHu | Factor FVII | Hemophilia | <1% |
| Benefix | Wyeth (Pfizer) | rHu | Factor IX | Hemophilia B | 3% |
| ATryn | GTC Biotherapeutics | rHu | Anti-thrombin | Thromboembolism | None reported |
| BabyBIG | California Department of Health Services | PD | Botulism Immune Globulin Intravenous Human | Infant botulism | |
| Berinert | CSL Behring | rHu | C1 Esterase Inhibitor | Angioedema | |
| Cinryze | Lev Pharmaceuticals | rHu | C1 Esterase Inhibitor | Angioedema | |
| Rhophylac | CSL Behring | PD | Rho(D) Immune Globulin | ITP | 0% (447) |
| Evithrom | OMRIX Biopharmaceuticals | rHu | Thrombin, Topical | Coagulation | 3.3% |
| Recothrom | ZymoGenetics | rHu | Thrombin, Topical | Coagulation | 1.2–1.5% |
| Wilate | Octapharma | PD | von Willebrand Factor | Coagulation | 1.5–3% |
| Cerezyme | Genzyme | rHu | β-glucocerebrosidase | Gaucher Disease | 15% |
| Exenatide or Byetta | Amylin Pharmaceuticals/Eli Lilly | R | Glucagon Like Peptide-1 | Type II diabetes | 6% |
| IntronA | Schering Corp (Bayer Schering Pharma) | rHu | IFNα | Leukemia, Kaposi sarcoma, hepatitis B/C | <3–13% |
| Betaseron | Bayer Schering Pharma | rHu | IFNβ | Multiple sclerosis | 16.5–25.2% |
| NovoLog | NovoNordisk | rHu | Insulin analog | Type II diabetes | Transient antibodies |
| Leukine | Genzyme | rHu | GM-CSF | Preventing infection in cancer | 2.3% |
| NEUPOGEN (Filgrastim) | Amgen | rHu | G-CSF | Preventing infection in cancer | 3% |
| Retavase | PDL Biopharma | rHu | TPA | Myocardial infarction, pulmonary embolism | 0% (2400) |
| Humatrope | Eli Lilly | rHu | Growth hormone | Dwarfism | 1.6% |
| Adagen | Enzon Pharmaceuticals | Bovine | ADA Adenosine deaminase | Inherited immunodeficiency | Not reported (SCID) |
| Pulmozyme | Genentech (Roche) | rHu | DNase I | Cystic fibrosis | 2–4% |
| Procrit | Amgen | rHu | EPO | Anemia in chronic renal disease | |
| Proleukin | Novartis | rHu | IL-2 | Oncology | <1% |

Recombinant human (rHu), plasma derived (PD) and recombinant (r) products are indicated. Companies that acquired a majority stake holding in any of the companies that performed the initial drug development of the biologics listed are shown in brackets

[FIG. 2]
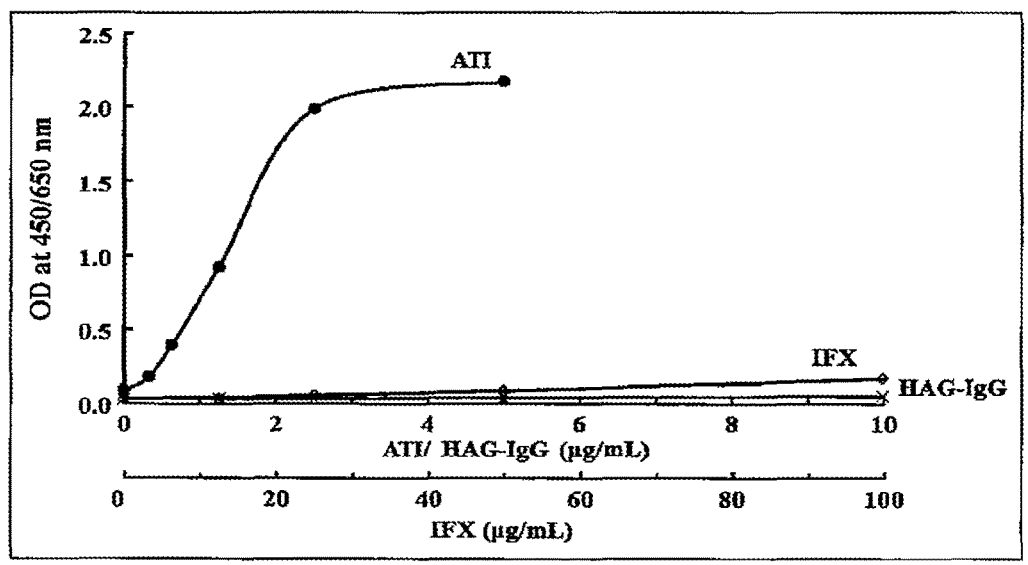
[FIG. 3]
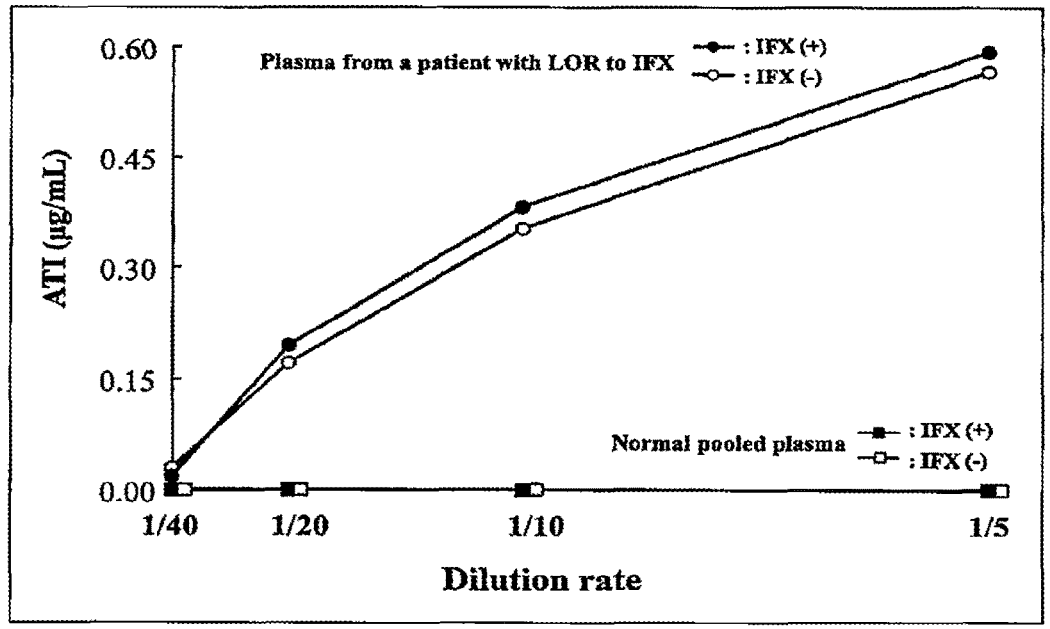

[FIG. 4]
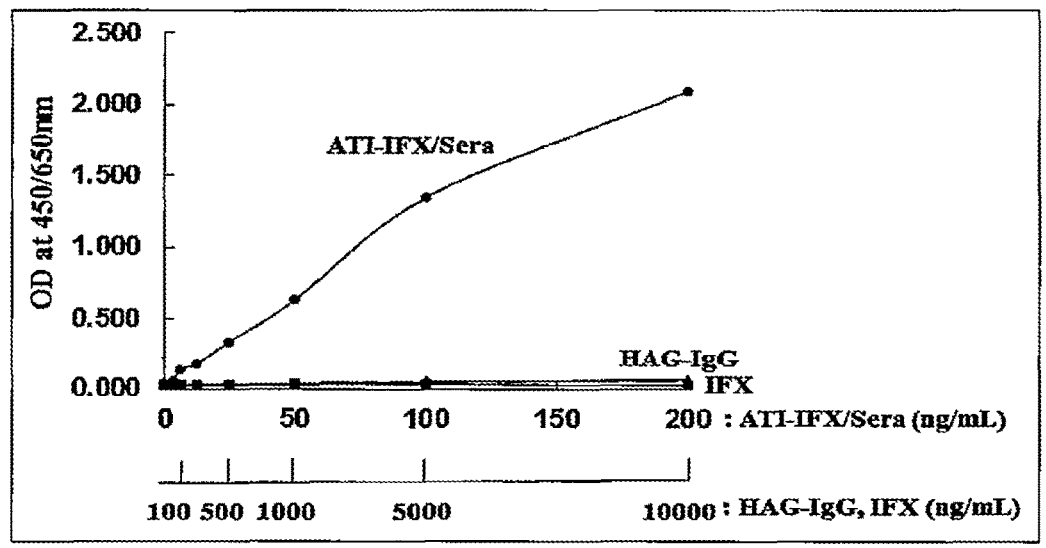
[FIG. 5]
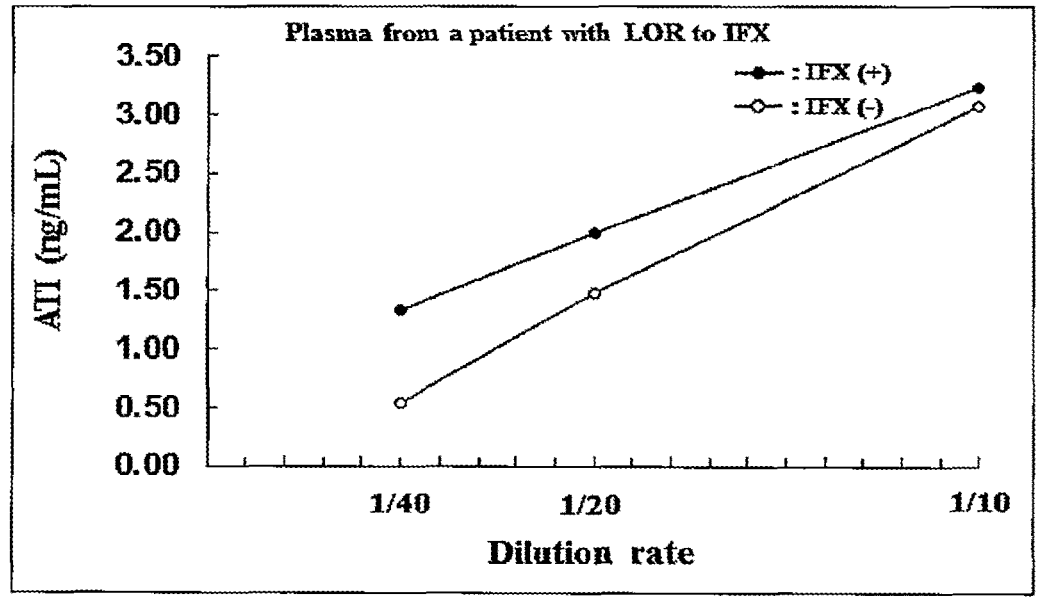

[FIG. 6]
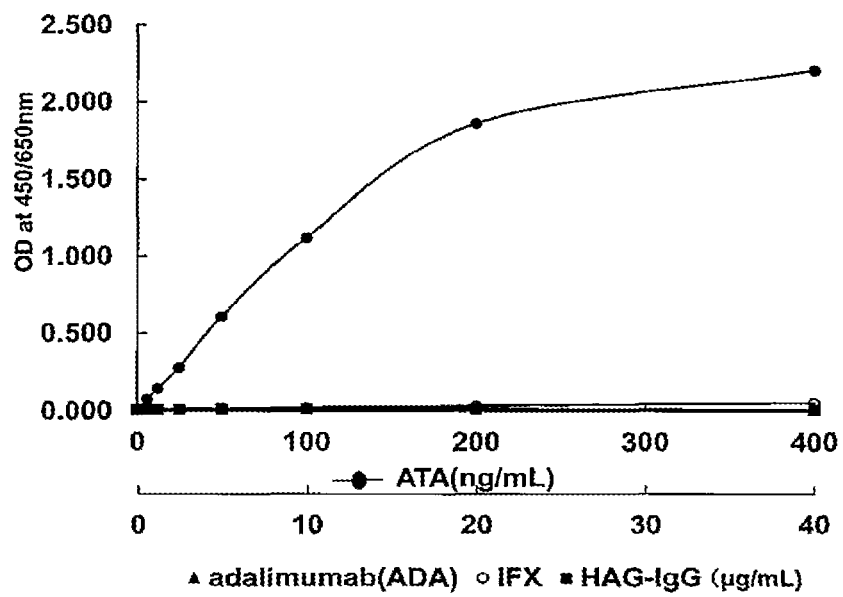
[FIG. 7]
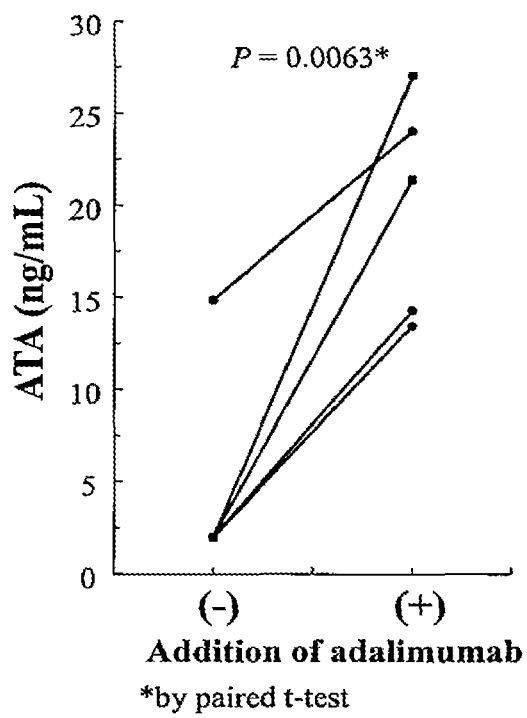

[FIG. 8]
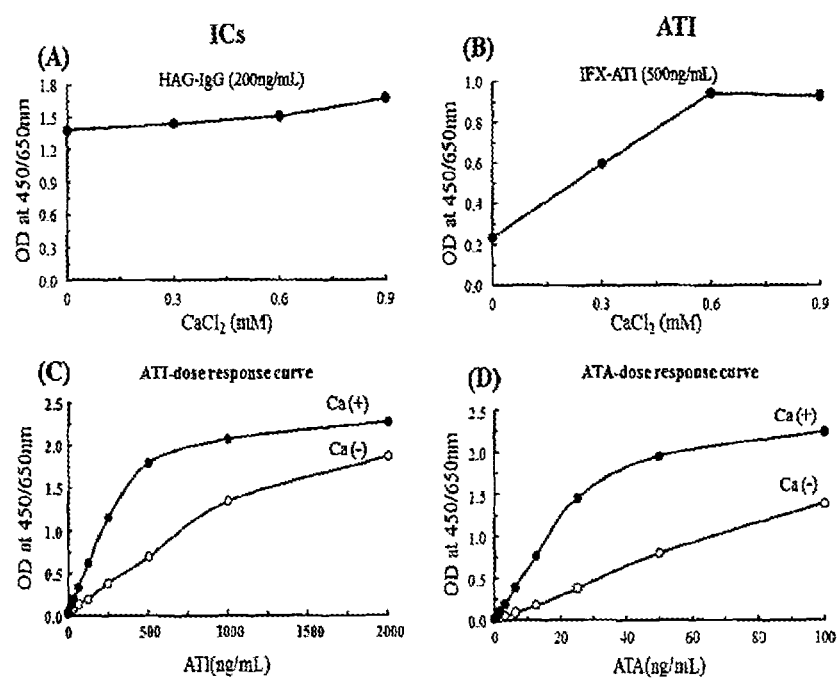

METHOD FOR MEASURING ANTI-DRUG ANTIBODY

FIELD OF THE INVENTION

The present invention relates to a method for detecting the presence or level of anti-drug antibodies (ADAs) in a sample.

BACKGROUND OF THE INVENTION

Biological drugs (hereinafter, referred to as "drugs") such as protein drugs, including antibody drugs, derived from a gene recombinant are drugs derived from an artificially produced antibody or substance specifically reactive with a disease-related molecule or receptor. Molecular-targeted treatment with a drug to control a targeted molecule or the like relating to the cause of a disease with pinpoint accuracy has become widely used in recent years, and currently 47 antibody drugs have been approved in Japan, U.S., and Europe. Most of them target cancers or autoimmune diseases, and quite a lot of products have become essential for treatment of such diseases.

However, antibody drugs induce production of ADAs due to the immune response of a patient to cause loss of response (LOR), even if the antibody drug is a humanized antibody or substance, which disadvantageously complicates disease control. Thus, required in the art is a measurement system to detect the presence of ADAs in a sample from a patient for monitoring of molecular-targeted therapy with a drug and guidance for therapeutic decision-making. Non-antibody drugs derived from a gene recombinant or the like, such as erythropoietin (Non Patent Literature 1), and other drugs also suffer from LOR or the like due to production of ADAs (Non Patent Literature 2).

In the case of infliximab (IFX), which is a representative antibody drug targeting TNF-α, for example, antibodies to IFX (ATI) appear after administration. Regarding measurement of ATI, an ATI measurement method by using double antigen assay with enzyme-linked immunosorbent assay (ELISA) (Non Patent Literature 3) and a mobility shift method in which a labeled IFX is added to a pre-treated sample and HPLC is used for the resultant (Non Patent Literature 4) are conventionally known.

However, the double antigen assay method, in which ATI are captured by IFX as a coating and the captured ATI are detected and measured with labeled IFX, may be influenced by IFX present in an analyte, which makes accurate measurement difficult. The mobility shift method requires introduction of HPLC, which is an expensive instrument, and thus is not easily applicable.

CITATION LIST

Non Patent Literature

[Non Patent Literature 1] Casadevall et al., N Engl J Med 2002; 346:469-475
[Non Patent Literature 2] Baker et al., Self/Nonself 2010; 1: 314-322
[Non Patent Literature 3] Uri Kopylov et al., Inflamm Bowel Dis 2012; 18:1628-1633
[Non Patent Literature 4] Wang S L et al., J Immunol Methods. 2012 Aug. 31; 382(1-2):177-88

SUMMARY OF THE INVENTION

Problems to be Solved by the Invention

The present invention relates to providing a method for measuring ADAs appearing in a patient receiving molecular-targeted therapy with a drug or maintenance administration of a recombinant cytokine, hormone, or the like in a simpler and more accurate manner.

Means for Solving the Problems

The present inventors investigated in view of such circumstances, and found that ADAs in an analyte to be measured can be measured accurately by allowing complement C1q or the like to capture ADAs present in an analyte in a form of a drug-ADAs immune complex, and detecting and measuring the captured drug-ADAs immune complex with an antibody to the corresponding drug.

Specifically, the present invention relates to the following [1] to [13].

[1] A method for measuring anti-drug antibodies (ADAs) in an analyte to be measured, the method comprising:
 (1) a step of providing a sample comprising an analyte to be measured for ADAs, the step comprising adding a corresponding drug to an analyte to be measured for ADAs to prepare a sample with a drug-ADAs immune complex formed;
 (2) a step of contacting the sample prepared in step (1) with a carrier coated with complement C1q, anti-C3d antibody, or anti-C1q antibody;
 (3) a step of contacting a labeled or non-labeled antibody to the drug corresponding to the ADAs with the coated carrier prepared in step (2); and
 (4) a step of quantifying the drug-ADAs immune complex binding to the complement C1q, anti-C3d antibody, or anti-C1q antibody.
[2] The method according to [1], wherein an amount of the drug to be added in step (1) is larger than an amount of the ADAs in the analyte to be measured.
[3] The method according to [1] or [2], wherein the drug is an anti-TNFα drug.
[4] The method according to [3], wherein the drug is infliximab, adalimumab, golimumab, or certolizumab pegol.
[5] The method according to any one of [1] to [4], wherein the drug is infliximab or adalimumab.
[6] The method according to any one of [1] to [5], wherein the antibody to the drug to be used in step (3) is a labeled antibody.
[7] The method according to [6], wherein the labeled antibody is an enzyme-labeled antibody.
[8] The method according to any one of [1] to [7], wherein the analyte to be measured is an analyte collected from a patient given the drug.
[9] An ADAs measurement kit for measuring ADAs by using the method according to any one of [1] to [8], the measurement kit comprising:
 a carrier coated with complement C1q, anti-C3d antibody, or anti-C1q antibody; and a labeled or non-labeled antibody to a drug corresponding to ADAs.
[10] The measurement kit according to [9], wherein the antibody to the drug is a labeled antibody.
[11] The measurement kit according to [10], further comprising the drug.

[12] A method for measuring ADAs in a sample, the method comprising:
a step of adding a corresponding drug to an analyte to be measured for ADAs to prepare a sample with a drug-ADAs immune complex formed;
a step of contacting the sample with complement C1q, anti-C3d antibody, or anti-C1q antibody; and
a step of quantifying the drug-ADAs immune complex binding to the complement C1q, anti-C3d antibody, or anti-C1q antibody.
[13] The method according to [12], wherein a labeled antibody to the drug is used in the step of quantifying.

Effects of the Invention

The method according to the present invention enables measurement of ADAs in an accurate and simple manner, without being influenced by a drug present in an analyte. Monitoring of ADAs by using the method according to the present invention enables determination of the presence or absence of the occurrence of LOR in molecular-targeted treatment with a drug or the like, and thus more suitable treatment can be provided.

BRIEF DESCRIPTION OF THE DRAWINGS

FIG. 1-A is a list of antibody drugs (document provided by Division of Biological Chemistry and Biologicals, National Institute of Health Sciences);

FIG. 1-B shows FDA-approved biological drugs except antibody drugs and the ADAs-developing rates of them (Baker et al., Self/Nonself 2010; 1; 314-322, Table 1);

FIG. 2 is a graph showing an ATI dose-response curve (ATI-C1q ELISA) and the specificity;

FIG. 3 is a graph showing the ATI concentration in each analyte, IFX(+): with addition of IFX, IFX(−): without addition of IFX;

FIG. 4 is a graph showing an ATI dose-response curve (ATI-Anti C3d MoAb ELISA) and the specificity;

FIG. 5 is a graph showing the ATI concentration in each analyte, IFX(+): with addition of IFX, IFX(−): without addition of IFX;

FIG. 6 is a graph showing an ATA dose-response curve (ATA-C1q ELISA) and the specificity;

FIG. 7 is a graph showing the ATA concentration in patient's plasma; increase in ATA concentration with addition of adalimumab (ADA) to plasma from 5 patients with inflammatory bowel disease who lost response to ADA.

FIG. 8 is a graph showing the influence of addition of calcium (Ca) in ADAs-C1q ELISA, (a) ICs-C1q ELISA measurement system, (b) ATI-C1q ELISA measurement system, (c) ATI-C1q ELISA dose-response curves, and (d) ATA-C1q ELISA dose-response curves.

DETAILED DESCRIPTION OF THE PREFERRED EMBODIMENTS

In the present invention, when the term "drug" is used simply, the term refers to one of biological drugs, including antibody drugs, derived from a gene recombinant.

Here, the term "antibody drug" refers to a drug comprising an artificially produced antibody which specifically binds to a disease-related molecule. Although the targeted molecule is not limited and various targeted molecules including cell surface molecules such as TNF-α, VEGF, and CD20 are contemplated, antibody drugs targeting TNF-α are suitable. Infliximab, adalimumab, golimumab, and certolizumab pegol are known to be antibody drugs targeting TNF-α, and infliximab is preferred among them.

Although any of mouse antibodies, chimeric antibodies, humanized antibodies, and human antibodies is applicable, humanized antibodies and human antibodies are preferred.

Antibody drugs approved in Japan, U.S., and Europe at the date of April 2016 are listed below. The details are shown in FIG. 1-A. FDA-approved biological drugs except antibody drugs are shown in FIG. 1-B.

Muromonab-CD3, ibritumomab tiuxetan, iodine 131 tositumomab, catumaxomab, blinatumomab, abciximab, rituximab, basiliximab, infliximab, cetuximab, brentuximab vedotin, siltuximab, dinutuximab, obiltoxaximab, daclizumab, palivizumab, trastuzumab, gemtuzumab ozogamic, alemtuzumab, omalizumab, efalizumab, bevacizumab, natalizumab, tocilizumab, ranibizumab, eculizumab, certolizumab pegol, mogamulizumab, pertuzumab, trastuzumab emtansine, obinutuzumab, vedolizumab, pembrolizumab, idarucizumab, mepolizumab, elotuzumab, daratumumab, ixekizumab, reslizumab, adalimumab, panitumumab, golimumab, ustekinumab, canakinumab, ofatumumab, denosumab, ipilimumab, belimumab, raxibacumab, ramucirumab, nivolumab, secukinumab, evolocumab, alirocumab, and necitumumab.

In the present invention, the term "ADAs" refers to antibodies which are produced when any of the above antibody drugs or any of the biological drugs except antibody drugs listed in FIG. 1-B is administered to a human, and recognize the drug.

The term "antibody drug" in the present invention refers to an antibody drug specified, and in this case ADAs refer to antibodies to the antibody drug specified. In the case of "infliximab (IFX)", examples of the ADAs include antibodies to infliximab (ATI: antibodies to infliximab).

Now, steps (1) to (4) in the method for measuring ADAs according to the present invention will be described.

<Step (1)>

This step is a step of providing a sample comprising an analyte to be measured for ADAs.

Here, an analyte to be measured refers to an analyte possibly containing ADAs, and for example, is an analyte collected from a patient given a drug. Preferred examples of the analyte to be measured include serum and plasma.

The analyte may be appropriately diluted, solubilized, or concentrated after being collected from a patient, in such a way that the measurement according to the present invention is not influenced thereby.

ADAs can be present in the body of a patient as a drug-ADAs immune complex formed by binding of a drug and ADAs, or as free ADAs. In the present invention, an excessive amount of a corresponding drug is added to an analyte to be measured for ADAs to prepare a sample with a drug-ADAs immune complex formed. Thereby, the total ADAs including free ADAs can be measured.

The sample can be prepared, specifically, by mixing and stirring a drug and an analyte together in an aqueous solvent, for example, an acid buffer solution (e.g., citrate buffer solution, phosphate buffer solution, Tris salt buffer solution, or acetate buffer solution, pH: approximately 5 to 9) to which a protein such as bovine serum albumin (BSA) and casein has been added.

The amount of a corresponding drug to be used may be any amount sufficient for recovering ADAs to the drug present in the analyte as an immune complex, and the amount of use is, for example, 2 to 10 μg, and preferably 3 to 5 μg per 100 μL of an analyte (serum or plasma).

The reaction time is typically 16 to 24 hours, and preferably 18 to 20 hours. The reaction temperature is preferably 4 to 10° C.

<Step (2)>

This step is a step of allowing a carrier coated with complement Clq, anti-C3d antibody, or anti-Clq antibody to capture the drug-ADAs immune complex in the sample.

The complement Clq, anti-C3d antibody, and anti-Clq antibody are each a molecule known to bind to an immune complex in the human blood flow.

The complement Clq, a protein of approximately 462 kDa composed of 18 subunits (six A-chains, six B-chains, and six C-chains), is a main configuration factor of the first factor Cl in the complement activation pathway, and recognizes an antigen-antibody complex (Sunyer, J. O. and Lambris, J. D. (1999). Complement. Encyclopedia of Life Sciences).

The Clq can be prepared by using a known method such as a method in which a crude Clq solution obtained by dialyzing serum or plasma is contacted with an IgG-coated insoluble carrier, and then the Clq adsorbed on the insoluble carrier is separated and collected (JP-A-H9-178745). Alternatively, commercially available Clq (e.g., Cat. No. C1740 from Sigma-Aldrich Co., LLC.) may be used.

The anti-Clq antibody is an antibody which recognizes the Clq, and is preferably a monoclonal antibody in the present invention. The anti-Clq monoclonal antibody is commercially available as MCA2603 from Bio-Rad AbD Serotec, Ltd., for example.

The anti-C3d antibody is an antibody which recognizes complement C3d, and is preferably a monoclonal antibody in the present invention. The anti-C3d monoclonal antibody is commercially available as MCA2648 from Bio-Rad AbD Serotec, Ltd., for example.

In coating of a carrier with Clq, anti-C3d or anti-Clq antibody, Clq, anti-C3d antibody, or anti-Clq antibody is fixed on a common insoluble, inert carrier.

Examples of such carriers include insoluble carriers in a form of beads, a microplate, a test tube, a stick, or test piece made of polystyrene, polycarbonate, polyvinyltoluene, polypropylene, polyethylene, polyvinyl chloride, nylon, polymethacrylate, latex, gelatin, agarose, cellulose, sepharose, glass, metal, ceramic, a magnetic substance, or the like.

Coating can be achieved by allowing Clq, anti-C3d antibody, or anti-Clq antibody to bind to a carrier by using a known method such as a physical adsorption method, a chemical bonding method, and combination of them. To coat a carrier with Clq, anti-C3d antibody, or anti-Clq antibody, for example, a Clq solution, anti-C3d antibody solution, or anti-Clq antibody solution, adjusted to have a concentration of 5 to 20 μg/mL with a buffer solution such as PBS (phosphate buffered saline), is contacted with a carrier, and reacted at 4 to 10° C. for 16 to 24 hours.

To inhibit non-specific binding to the carrier, it is preferred in typical cases to perform blocking treatment after the completion of the reaction by using a blocking solution containing a protein such as bovine serum albumin (BSA) and casein and a surfactant such as Tween® 20 (polysorbate 20).

Contact of a sample with the coated carrier can be achieved by reacting, for example, at 4 to 10° C. for 16 to 24 hours.

After the completion of the reaction, the resultant is washed with a buffer solution or the like containing a surfactant such as Tween® 20 (polysorbate 20) to remove unreacted substances.

<Step (3)>

This step is a step of contacting a labeled or non-labeled antibody to the drug corresponding to the ADAs (ADAs for detection) with the coated carrier prepared in step (2), and thereby reacting with the drug-ADAs immune complex binding to the Clq, anti-C3d antibody, or anti-Clq antibody.

Here, the labeled or non-labeled antibody to the drug corresponding to the ADAs may be a monoclonal antibody or polyclonal antibody which recognizes the drug (drug corresponding to ADAs to be measured), and such an antibody can be obtained by using a common method for producing an antibody. For the antibody, not only IgG but also a fragment of an antibody (e.g., F(ab')$_2$ fragment, Fab' fragment, etc.) may be used.

To obtain a polyclonal antibody, for example, a mammal is immunized with a drug as an antigen, and blood is collected from the mammal, and an antibody is then separated and purified from the collected blood. Immunization can be administered to a mammal such as a mouse, hamster, Guinea pig, chicken, rat, rabbit, dog, goat, sheep, and cattle. The method for administration of an antigen is known to those skilled in the art, and the route of administration is not limited, and may be appropriately chosen from subcutaneous administration, intradermal administration, intraperitoneal administration, intravenous administration, intramuscular administration, and so on. In addition, an adjuvant may be used, as necessary. After the immunized mammal is kept for an appropriate period, a small quantity of the serum is sampled, for example, from the ear vein of the mammal, and the antibody titer is measured. If the antibody titer becomes higher, an antigen may be administered for booster immunization in accordance with the situation. One to two months after the final administration of antigen, blood is collected from the immunized animal by using a common method, and the blood is separated and purified by using a common method such as centrifugation, precipitation with ammonium sulfate or polyethylene glycol, and chromatography such as gel filtration chromatography, ion-exchange chromatography, and affinity chromatography, and thus polyclonal ADAs can be obtained as polyclonal antiserums.

To obtain a monoclonal antibody, for example, a hybridoma is produced through cell fusion of an antibody-producing cell and a myeloma cell line. Examples of applicable antibody-producing cells include splenocytes, lymph node cells, and B-lymphocytes from an immunized animal.

To produce a hybridoma, for example, a splenocyte as an antibody-producing cell is obtained from an immunized animal, and the splenocyte is fused with a myeloma cell by using a known method (G. Kohler et al., Nature, 256, 495(1975)). Examples of myeloma cell strains for cell fusion include, in the case of a mouse, P3X63Ag8, cell line P3U1, and cell line Sp2/0. A fusion accelerator such as polyethylene glycol and a Sendai virus can be used for cell fusion, and a hypoxanthine-aminopterin-thymidine (HAT) medium can be used for selection of a hybridoma after cell fusion in accordance with a conventional method. The hybridoma obtained through cell fusion is cloned by using a limiting dilution method or the like.

Screening is further performed by using enzyme immunoassay with drugs, and thus a cell line to produce a monoclonal antibody which specifically recognizes a drug of interest can be obtained. To produce an intended monoclonal antibody from a hybridoma, the hybridoma is cultured by using a common cell culture method or an ascites formation method, and the monoclonal antibody can be suitably purified from the culture supernatant or ascites. Purification of the monoclonal antibody from the culture supernatant or ascites can be performed in accordance with a conventional method. For example, ammonium sulfate fractionation, gel filtration, ion-exchange chromatography, affinity chromatography, etc., may be appropriately used in combination.

For antibody drugs listed in the following Table 1, the monoclonal antibodies to the antibody drugs are commercially available from Bio-Rad AbD Serotec, Ltd. (Oxford, UK), and the commercial products may be used in the present invention.

<Step (4)>

This step is a step of quantifying the drug-ADAs immune complex binding to the C1q, anti-C3d antibody, or anti-C1q antibody through measurement of the amount of antibodies to a drug involving in binding to the drug-ADAs immune complex.

Measurement of the amount of antibodies to a corresponding drug, i.e., ADAs can be performed by using a known immunoassay. Representative immunoassay is

TABLE 1

| | Antibody drug | Trade name | Targeted molecule | Main indications | MoAb product code |
|---|---|---|---|---|---|
| 1 | Infliximab | Remicade | TNFα | ulcerative colitis, Crohn's disease, rheumatoid arthritis | HCA216P |
| 2 | Adalimumab | Humira | TNFα | ulcerative colitis, Crohn's disease, rheumatoid arthritis | HCA232P |
| 3 | Golimumab | Simponi | TNFα | ulcerative colitis, Crohn's disease, rheumatoid arthritis | HCA243 |
| 4 | Tocilizumab | Actemra | IL-6R | rheumatoid arthritis, Castleman's disease | HCA257P |
| 5 | Ustekinumab | Stelara | IL-12, IL-23-p40 | psoriasis | HCA210P |
| 6 | Omalizumab | Xolair | IgE | asthma | HCA235P |
| 7 | Natalizumab | Tysabri | α4 integrin | multiple sclerosis | HCA249P |
| 8 | Rituximab | Rituxan | CD20 | B-cell non-Hodgkin's lymphoma | MCA2260P |
| 9 | Alemtuzumab | Campath | CD52 | B-cell chronic lymphocytic leukemia | HCA175P |
| 10 | Cetuximab | Erbitux | EGFR | head and neck cancer, colorectal cancer | HCA228P |
| 11 | Bevacizumab | Avastin | VEGF | colorectal cancer | HCA184P |
| 12 | Panitumumab | Vectibix | EGFR | colorectal cancer | HCA265 |
| 13 | Palivizumab | Synagis | RSV F protein | RS virus infection | HCA262P |
| 14 | Trastuzumab | Herceptin | HER2 | metastatic breast cancer | HCA176P |

In the case that a labeled form (labeled ADAs) is used for the ADAs for detection, for example, an enzyme, a radioisotope, or a fluorescent substance conventionally used for immunoassay can be used for a label. However, an enzyme is preferably used. Examples of such enzymes include alkaline phosphatase (ALP), peroxidase (HRP), β-galactosidase, urease, catalase, glucose oxidase, lactate dehydrogenase, microperoxidase, chymotrypsinogen, procarboxypeptidase, glyceraldehyde-3-phosphate dehydrogenase, amylase, phosphorylase, D-nase, and P-nase.

Examples of the radioisotope include tritium, $^{125}$iodine, and $^{131}$iodine, and examples of the fluorescent substance include fluorescein isothiocyanate (FITC), tetramethylrhodamine isothiocyanate (RITC), substituted rhodamine isothiocyanate, dichlorotriazine isothiocyanate, Alexa, and AlexaFluoro.

Labeling with these labeling materials can be performed in accordance with a known method.

In adding labeled ADAs to a coated carrier, it is preferred to add labeled ADAs diluted with a buffer containing a protein such as bovine serum albumin (BSA) and casein and a surfactant such as Tween® 20 (polysorbate 20) (e.g., Can Get Signal Solution 2 (Cat. No. NKB-301, TOYOBO CO., LTD.)). From the viewpoint of enhancement of detection sensitivity for an antigen molecule (drug) in an immune complex derived from ADAs, it is preferred to add calcium ions such as $CaCl_2$ to the buffer.

The reaction (binding) conditions are not limited, and common conditions typically used for such measurement methods are employed. In typical cases, the reaction can be suitably performed, generally at 45° C. or below, preferably at room temperature, for approximately 1 to 5 hours.

After the completion of the reaction, the resultant is washed with a buffer solution containing a surfactant such as Tween® 20 (polysorbate 20) to remove unreacted labeled ADAs.

enzyme immunoassay (ELISA), and examples of immunoassays further include the following measurement methods.
1. Chemiluminescence method: MSD: Electrochemiluminescence was measured on the Sector Imager 6000 instrument (Meso Scale Discovery, Rockville, Md., United States).
2. Immunochromatography: HMSA (homogeneous mobility shift assay): Agilent Technologies 1200 series HPLC system (Santa Clara, Calif.). BioSep SEC-3000 column (Phenomenex, Inc., Torrance, Calif.).
3. BIAcore (Plasmon Resonance): Biacore T100 Immunogenicity Package (GE Healthcare Bio-Sciences Gyros AB, Uppsala Sweden).
4. Fluorescence Method:
    4-1 Gyrolab. Fluorescence was measured on the Gyrolab Workstation with the Gyrolab Control software (v5.4.0) (Gyros AB, Uppsala, Sweden).
    4-2 AlphaLISA. Fluorescence was measured on the Synergy NEO instrument (BioTek Instruments, Inc., Luzern, Switzerland).
5. Radioimmunoassay (RIA)
6. Immunoradiometric Assay (IRMA)
7. Fluorescence Polarization Immunoassay (FPIA)
8. Immunoturbidimetry (Immunonephelometry)
9. Latex Agglutination Turbidimetry
10. Latex Agglutination Inhibition Immunoassay
11. Time-Resolved Fluorescence Immunoassay (TR-FIA)

In the case that a labeled antibody is used as an antibody to a drug, for example, the amount of a labeled form is measured, and the measurement of a labeled form is performed by using a method according to the label. Specifically, the enzyme activity is measured for an enzyme label, the radioactivity is measured for a radioactive label, and the fluorescence intensity is measured for a fluorescent label.

For example, TMB (3,3',5,5'-tetramethylbenzidine) is used as a substrate in the case that peroxidase is used as a labeling enzyme, or p-nitrophenyl phosphate is used as a substrate in the case that alkaline phosphatase is used, and the decomposition of the substrate can be measured by using a spectrophotometer or the like.

The amount of ADAs in an analyte is calculated from the value quantified for a drug-ADAs immune complex contained in a sample, on the basis of a calibration curve determined from measurement values for a drug-ADAs immune complex formed in reference samples.

The method according to the present invention enables measurement for ADAs binding to a drug and/or free ADAs not binding to a drug, present in an analyte.

A kit according to the present invention is a measurement kit for ADAs, the kit comprising: a carrier at least coated with C1q, anti-C3d antibody, or anti-C1q antibody; and a labeled antibody to a corresponding drug. The kit can be preferably a kit for performing the above-described method for measuring ADAs.

The kit according to the present invention may further comprise a drug specified in the present invention, and may additionally comprise, for example, a substrate for detection of a labeling material, a reagent necessary for measurement, a diluting solution, a buffer solution, or a washing solution, as necessary.

As described above, the present invention is based on, as a measurement principle, quantification of ADAs of interest derived from a patient through capturing ADAs in the sample as a drug-ADAs immune complex and use of ADAs for detection. Although, in the following Examples, quantification of ADAs by using ELISA will be illustrated in which a drug-ADAs immune complex is captured on complement C1q or anti-C3d antibody as a coating, a gene recombinant, complement receptor, monoclonal antibody, or the like, capable of capturing C1q or a similar immune complex may be used. For the immunoassay, the above-mentioned various immunoassays, automated analyzers, and the like, may be used in addition to ELISA. Thus, the present invention is never limited to Examples.

EXAMPLES

Example 1: Measurement of Antibodies to Infliximab (IFX) (ATI) <1>

<Preparation of Reagents>
1) PBS (Phosphate Buffered Saline);
PBS(−): NaCl 137 mmol/L, KCl 2.68 mmol/L, KHPO$_4$ 2 mmol/L, NaH$_2$PO$_4$.12H$_2$O 10 mmol/L, pH 7.4
PBS(+): prepared by adding 0.9 mM of CaCl$_2$ and 0.33 mM of MgCl$_2$.12H$_2$O to PBS(−)
2) Blocking Buffer;
To PBS(−), 0.5% boiled (for 5 minutes) casein (Cat. No. C7078, Sigma-Aldrich Co., LLC.), 1% Tween® 20 (polysorbate 20), and 0.01% thimerosal were added.
1. Preparation of C1q-Coated Plate
(1) C1q (Cat. No. C1740, Sigma-Aldrich Co., LLC.) adjusted to have a concentration of 10 μg/mL with PBS(−) was dispensed in an amount of 100 μL into each well of a 96-well ELISA plate (MaxisorpF8 x12, Cat. No. 468667, Nunc), and the plate was left to stand at 4° C. overnight.
(2) The C1q solutions in the plate were discarded, and each well was washed once with 300 μL of PBS(−) containing 0.5% Tween® 20 (polysorbate 20).
(3) After washing, 300 μL of the blocking buffer was added, and reacted at room temperature for 1 hour. After the reaction, the solutions were discarded, and the plate was dried in air flow for 2 hours, and thus a C1q-coated plate was prepared.

2. Preparation of Samples
(1) Preparation of Reference Samples
1) Anti-human IgG antibodies were used as a substitute for antibodies to IFX (ATI) reference samples.
The concentration of rabbit anti-human IgG (H+L) antibodies (Cat. No. ab7155, Abcam plc.) was adjusted to 5 μg/mL with PBS(+) containing 0.1% BSA (Cat. No. A-3803, Sigma-Aldrich Co., LLC.), and serial dilution was further performed with 0.1% BSA-containing PBS(+) to prepare reference materials having concentrations of 0.078 μg/mL, 0.156 μg/mL, 0.312 μg/mL, 0.625 μg/mL, 1.25 μg/mL, and 2.5 μg/mL, respectively.
2) Each of the reference materials having the respective concentrations in a volume of 200 μL was put in a microtube, and thereto 50 μL of IFX (62.5 μg/mL; Mitsubishi Tanabe Pharma Corporation) diluted with 0.1% BSA-containing PBS(+) was added to be mixed together, and thereafter the resultant was reacted at 4° C. overnight, and thus reference materials (IFX-ATI immune complex) were prepared.
(2) Preparation of IFX Solutions
IFX cryopreserved at a concentration of 1 mg/mL was thawed, and serially diluted with 0.1% BSA-containing PBS(+) to prepare IFX solutions having concentrations of 12.5 μg/mL, 25 μg/mL, 50 μg/mL, and 100 μg/mL, respectively.
(3) Preparation of Heat Aggregated Human IgG (HAG-IgG) Solutions
Human IgG (14506, Sigma-Aldrich Co., LLC.) at a concentration of 5 mg/mL was heated at 63° C. for 20 minutes, and centrifuged at 10,000×g for 5 minutes, and the supernatant was then collected, and thus HAG-IgG was prepared. The HAG-IgG was diluted to 10 μg/mL with 0.1% BSA-containing PBS(+), and further serially diluted to prepare HAG-IgG solutions having concentrations of 1.25 μg/mL, 2.5 μg/mL, 5.0 μg/mL, and 10 μg/mL, respectively.
3. Immunoassay (ATI-C1q ELISA)
(1) The reference materials prepared in the above 2(1), the IFX solutions prepared in the above 2(2), and the HAG-IgG solutions prepared in the above 2(3) were each dispensed in an amount of 100 μL into each well of the C1q-coated plate, and reacted at room temperature for 1 hour with stirring by using a plate mixer.
(2) Subsequently, the reaction solutions were discarded, and a procedure in which 300 μL of PBS(−) containing 0.5% Tween® 20 (polysorbate 20) (Cat. No. 1706531, Bio-Rad Laboratories, Inc.) was added to each well, and the solution was then discarded, was repeated four times to wash each well.
(3) HRP-labeled human anti-IFX monoclonal antibody (Cat. No. HCA216P, Bio-Rad AbD Serotec, Ltd.) was diluted by 1,000-fold with Can Get Signal Solution 2 (Cat. No. NKB-301, TOYOBO CO., LTD.), and the resultant was dispensed in an amount of 100 μL into each well, and reacted at room temperature for 1 hour with stirring by using a plate mixer.
(4) After the reaction, the solutions were discarded, and a procedure in which 300 μL of 0.5% Tween® 20 (polysorbate 20)-containing PBS(−) was added to each well, and the solution was then discarded, was repeated four times to wash each well.
(5) A TMB Blue substrate solution (Cat. No. S1601, Dako) in a volume of 100 μL was added to each well, and the resultant was stirred, and then left to stand at room temperature under shaded conditions for 30 minutes.
(6) After development of color, 50 μL of 1N-H$_2$SO$_4$ was added to each well to terminate the reaction, and the optical density was measured at wavelengths of 450 nm/650 nm by using a plate reader (absorptiometer for 96-well plates).

(7) The calibration curve (dose-response curve) of the reference sample was determined.

4. Results

At 2.5 µg/mL of ATI, the optical density (O.D.) was 1.99, and the dose-response curve reached a plateau (FIG. 2). In contrast, clear increase of O.D. was not found even when the HAG-IgG to be captured by the C1q was added at a concentration of 10 µg/mL or IFX was added at a concentration of 100 µg/mL.

Accordingly, the amount of ATI in an analyte can be specifically calculated from the optical density of the analyte on the basis of the dose-response curve (calibration curve).

Example 2: Measurement of Antibodies to Infliximab (ATI) in Plasma from Patient <1>

1. Preparation of Samples (1) Plasma collected from a patient who had experienced the occurrence of loss of response (LOR) to the antibody drug was diluted by 4-fold with PBS(+), and the diluted plasma was dispensed in an amount of 200 µL into a microtube, and 50 µL of IFX (62.5 µg/mL) diluted with 0.1% BSA-containing PBS(+) or 50 µL of 0.1% BSA-containing PBS(+) was further added thereto to be mixed together, and the resultant was then reacted at 4° C. overnight (final dilution rate: 5-fold).

(2) An analyte of normal pooled plasma prepared by mixing plasma samples derived from five healthy individuals was diluted by 4-fold with PBS(+) in the same manner as preparation of the analyte from a patient, and the diluted plasma was dispensed in an amount of 200 µL into a microtube, and 50 µL of IFX (62.5 µg/mL) diluted with 0.1% BSA-containing PBS(+) or 50 µL of 0.1% BSA-containing PBS(+) was further added thereto to be mixed together, and the resultant was then reacted at 4° C. overnight (final dilution rate: 5-fold).

2. Immunoassay

The samples prepared in the above 1(1) and 1(2) were each dispensed in an amount of 100 µL into each well of a C1q-coated plate prepared in the same manner as in Example 1, and reacted in accordance with the method illustrated in 3. Immunoassay in Example 1, and then the amount of ATI in each sample was determined on the basis of the calibration curve shown in FIG. 2.

3. Results

For the plasma from a patient, addition of IFX further promoted formation of IFX-ATI immune complexes to result in a larger measurement value, and lower measurement values were obtained as the dilution rate was higher. For the analyte of normal plasma, on the other hand, ATI were not detected regardless whether IFX were added or not (FIG. 3).

From these results, it was found that the method based on addition of IFX according to the present invention allows measurement of the amounts or amount of ATI binding to IFX and/or ATI not binding to IFX contained in the plasma of a patient.

Example 3: Measurement of Antibodies to Infliximab (IFX) (ATI) <2>

<Preparation of Reagents>

1) PBS (Phosphate Buffered Saline);

PBS(−): NaCl 137 mmol/L, KCl 2.68 mmol/L, KHPO$_4$ 2 mmol/L, NaH$_2$PO$_4$.12H$_2$O 10 mmol/L, pH 7.4

PBS(+): prepared by adding 0.9 mM of CaCl$_2$ and 0.33 mM of MgCl$_2$.12H$_2$O to PBS(−)

2) Blocking Buffer;

To PBS(−),0.5% boiled (for 5 minutes) casein (Cat. No. C7078, Sigma-Aldrich Co., LLC.), 1% Tween® 20 (polysorbate 20), and 0.01% thimerosal were added.

1. Preparation of Anti-Cd3 Monoclonal Antibody-Coated Plate (1) Anti-Cd3 monoclonal antibodies (Anti-C3d MoAb; Cat. No. MCA2648, Bio-Rad AbD Serotec, Ltd.) adjusted to have a concentration of 1 µg/mL with PBS(−) were dispensed in an amount of 100 µL into each well of a 96-well ELISA plate (MaxisorpF8 x12, Cat. No. 468667, Nunc), and the plate was left to stand at 4° C. overnight. Thereafter, the plate was washed once.

(2) After washing, 300 µL of the blocking buffer was added thereto, and the resultant was reacted at room temperature for 1 hour. After the reaction, the solutions were discarded, and the plate was dried in air flow for 2 hours, and thus an anti-Cd3 monoclonal antibody-coated plate was prepared.

2. Preparation of Samples (1) Preparation of Reference Materials (IFX-ATI Immune Complex (ATI-IFX/Sera))

1) IFX at a concentration of 100 µg/100 µL/tube and rabbit anti-human IgG (H+L) antibodies (as a substitution for ATI) at a concentration of 100 µg/100 µL each cryopreserved were mixed together, and reacted at 4° C. for 18 hours.

2) After the reaction, 800 µL of 62% pooled serum from healthy individuals (diluted with saline) was added thereto to reach a concentration of 100 µg/mL, and the resultant was reacted at 37° C. for 60 minutes.

3) After the completion of the reaction, the resultant was diluted by 20-fold with 0.1% BSA/0.01% thimerosal/PBS (+) to reach a concentration of 5 µg/mL, and thus an ATI reference solution was obtained. The ATI reference solution was dispensed at 500 µL/tube, and cryopreserved at −80° C.

4) The ATI reference solution (5 µg/mL) after cryopreservation was thawed and 40 µL thereof was taken, to which 960 µL of 0.1% BSA/0.01% thimerosal/PBS(+) was added to reach 200 ng/mL. Further, serial dilution was performed repeatedly to prepare reference materials (ATI-IFX/Sera) having concentrations of 0 ng/mL, 3.125 ng/mL, 6.25 ng/mL, 12.5 ng/mL, 25 ng/mL, 50 ng/mL, 100 ng/mL, and 200 ng/mL, respectively.

(2) Preparation of IFX Solutions

IFX cryopreserved at a concentration of 1 mg/mL was thawed, and serially diluted with 0.1% BSA-containing PBS(+) to prepare IFX solutions having concentrations of 0.1 µg/mL, 0.5 µg/mL, 1 µg/mL, 5 µg/mL, and 10 µg/mL, respectively.

(3) Preparation of Heat Aggregated Human IgG (HAG-IgG) Solutions

Human IgG (14506, Sigma-Aldrich Co., LLC.) at a concentration of 5 mg/mL was heated at 63° C. for 20 minutes, and centrifuged at 10,000×g for 5 minutes, and the supernatant was then collected, and thus HAG-IgG was prepared. The HAG-IgG was diluted to 10 µg/mL with 0.1% BSA-containing PBS(+), and further serially diluted to prepare HAG-IgG solutions having concentrations of 0.1 µg/mL, 0.5 µg/mL, 1 µg/mL, 5 µg/mL, and 10 µg/mL, respectively.

3. Immunoassay (ATI-Anti C3d MoAb ELISA)

(1) The reference materials were dispensed in an amount of 100 µL into each well of the anti-Cd3 monoclonal antibody-coated plate, and reacted at room temperature for 1 hour with stirring by using a plate mixer.

(2) Subsequently, the reaction solutions were discarded, and a procedure in which 300 μL of PBS(−) containing 0.5% Tween® 20 (polysorbate 20) (Cat. No. 1706531, Bio-Rad Laboratories, Inc.) was added to each well, and the solution was then discarded, was repeated four times to wash each well.

(3) HRP-labeled human anti-IFX monoclonal antibody (Cat. No. HCA216P, Bio-Rad AbD Serotec, Ltd.) was diluted by 1,000-fold with Can Get Signal Solution 2 (Cat. No. NKB-301, TOYOBO CO., LTD.), and the resultant was dispensed in an amount of 100 μL into each well, and reacted at room temperature for 1 hour with stirring by using a plate mixer.

(4) After the reaction, the solutions were discarded, and a procedure in which 300 μL of 0.5% Tween® 20 (polysorbate 20)-containing PBS(−) was added to each well, and the solution was then discarded, was repeated four times to wash each well.

(5) After washing, a TMB Blue substrate solution (Cat. No. 51601, Dako) in a volume of 100 μL was added to each well, and the resultant was reacted at room temperature under shaded conditions for 15 to 30 minutes.

(6) After development of color, 50 μL of 1.0 M $H_2SO_4$ was added to terminate the reaction, and the optical density was measured at two wavelengths of 450 nm/650 nm by using a plate reader (absorptiometer for 96-well plates).

(7) The calibration curve (dose-response curve) of the reference material was determined.

4. Results

In the dose-response curve, the optical density (O.D.) reached a maximum value of 2.1 at 200 ng/mL of ATI. In contrast, clear increase of O.D. was not found even when the human IgG agglutinating through heating (HAG-IgG) to bind to the C3d was added at a concentration of 10 μg/mL or IFX was added at a concentration of 10 μg/mL (FIG. 4).

Example 4: Measurement of Antibodies to Infliximab (ATI) in Plasma from Patient <2>

1. Preparation of Samples

To 120 μL of plasma collected from a patient with ulcerative colitis who had experienced the occurrence of LOR during IFX maintenance therapy, 360 μL of 0.1% BSA/0.01% thimerosal/PBS(+) was added to dilute by 4-fold, and the diluted plasma was dispensed in an amount of 200 μL into each of two microtubes, and 50 μL of IFX (125 μg/mL) prepared with 0.1% BSA/0.01% thimerosal/PBS(+) or 50 μL of 0.1% BSA/0.01% thimerosal/PBS(+) was further added thereto to be mixed together, and the resultant was then reacted at 4° C. overnight (dilution rate: 10-fold to 40-fold).

2. Immunoassay

The samples prepared in the above 1 were each dispensed in an amount of 100 μL into each well of an anti-Cd3 monoclonal antibody-coated plate prepared in the same manner as in Example 3, and reacted in accordance with the method illustrated in 3. Immunoassay in Example 3 and then the amount of ATI in the samples was determined on the basis of the calibration curve shown in FIG. 4.

3. Results

For the plasma from a patient, addition of IFX further promoted formation of IFX immune complexes to result in a larger measurement value, and lower measurement values were obtained as the dilution rate was higher (FIG. 5).

Example 5: Measurement of Antibodies to Adalimumab (ATA) <1>

<Preparation of Reagents>
1) PBS (Phosphate Buffered Saline);
PBS(−): NaCl 137 mmol/L, KCl 2.68 mmol/L, $KHPO_4$ 2 mmol/L, $NaH_2PO_4 \cdot 12H_2O$ 10 mmol/L, pH 7.4
PBS(+): prepared by adding 0.9 mM of $CaCl_2$ and 0.33 mM of $MgCl_2 \cdot 12H_2O$ to PBS(−)
2) Blocking Buffer;
To PBS(−),0.5% boiled (for 5 minutes) casein (Cat. No. C7078, Sigma-Aldrich Co., LLC.), 1% Tween® 20 (polysorbate 20), and 0.01% thimerosal were added.
3) Diluent;
Prepared by adding 0.1% BSA and 0.01% thimerosal to PBS(+).

1. Preparation of C1q-Coated Plate (1) C1q (Cat. No. C1740, Sigma-Aldrich Co., LLC.) adjusted to have a concentration of 10 μg/mL with PBS(−) was dispensed in an amount of 100 μL into each well of a 96-well ELISA plate (MaxisorpF8 x12, Cat. No. 468667, Nunc), and the plate was left to stand at 4° C. overnight.

(2) The C1q solutions in the plate was discarded, and each well was washed once with 300 μL of PBS(−) containing 0.5% Tween® 20 (polysorbate 20).

(3) After washing, 300 μL of the blocking buffer was added, and reacted at room temperature for 1 hour. After the reaction, the solutions were discarded, and the plate was dried in air flow for 2 hours, and thus a C1q-coated plate was prepared.

2. Preparation of Samples (1) Preparation of Reference Samples

1) Anti-human IgG antibodies were used as a substitute for antibodies to ADA (ATA) reference samples.

The concentration of rabbit anti-human IgG (H+L) antibodies (Cat. No. ab7155, Abcam plc.) was adjusted to 400 ng/mL with the diluent, and serial dilution was further performed with the diluent to prepare reference materials having concentrations of 6.25 ng/mL, 12.5 ng/mL, 25 ng/mL, 50 ng/mL, 100 ng/mL, 200 ng/mL, and 400 ng/mL, respectively.

2) Each of the reference materials having the respective concentrations in a volume of 200 μL was put in a microtube, and thereto 50 μL of adalimumab (ADA, 125 μg/mL; Eisai Co., Ltd.) diluted with the diluent was added to be mixed together, and thereafter the resultant was reacted at 4° C. overnight, and thus reference materials (ATA-ADA immune complexes) were prepared.

(2) Preparation of Adalimumab Solutions and IFX Solutions

IFX and adalimumab each cryopreserved at a concentration of 1 mg/mL were thawed, and serially diluted with the diluent to prepare IFX solutions and adalimumab solutions having concentrations of 1.25 μg/mL, 2.5 μg/mL, 5 μg/mL, 10 μg/mL, 20 μg/mL, and 40 μg/mL, respectively.

(3) Preparation of Heat Aggregated Human IgG (HAG-IgG) Solutions

Human IgG (14506, Sigma-Aldrich Co., LLC.) at a concentration of 5 mg/mL was heated at 63° C. for 20 minutes, and centrifuged at 10,000×g for 5 minutes, and the supernatant was then collected, and thus HAG-IgG was prepared. The HAG-IgG was diluted to 40 μg/mL with the diluent, and further serially diluted to prepare HAG-IgG solutions having concentrations of 1.25 µg/mL, 2.5 µg/mL, 5.0 µg/mL, 10 µg/mL, 20 µg/mL, and 40 µg/mL, respectively.

3. Immunoassay (ATA-Clq ELISA)

(1) The reference materials prepared in the above 2(1) were dispensed in an amount of 100 µL into each well of the Clq-coated plate, and reacted at 25° C. for 2 hours with stirring by using a plate mixer.

(2) Subsequently, the reaction solutions were discarded, and a procedure in which 300 µL of PBS(−) containing 0.5% Tween® 20 (polysorbate 20) (Cat. No. 1706531, Bio-Rad Laboratories, Inc.) was added to each well, and the solution was then discarded, was repeated four times to wash each well.

(3) HRP-labeled human anti-adalimumab monoclonal antibody (Cat. No. HCA204P, Bio-Rad AbD Serotec, Ltd.) was diluted by 2,000-fold with Can Get Signal Solution 2 (Cat. No. NKB-301, TOYOBO CO., LTD.), and the resultant was dispensed in an amount of 100 µL into each well, and reacted at room temperature for 1 hour with stirring by using a plate mixer.

(4) After the reaction, the solutions were discarded, and a procedure in which 300 µL of 0.5% Tween® 20 (polysorbate 20)-containing PBS(−) was added to each well, and the solution was then discarded, was repeated four times to wash each well.

(5) A TMB Blue substrate solution (Cat. No. S1601, Dako) in a volume of 100 µL was added to each well, and the resultant was stirred, and then left to stand at room temperature under shaded conditions for 30 minutes.

(6) After development of color, 50 µL of $1N-H_2SO_4$ was added to each well to terminate the reaction, and the optical density was measured at wavelengths of 450 nm/650 nm by using a plate reader (absorptiometer for 96-well plates).

(7) The calibration curve (dose-response curve) of the reference sample was determined.

4. Results

At 200 ng/mL of ATA, the optical density (O.D.) was 1.863, and the dose-response curve reached a plateau (FIG. 6). In contrast, clear increase of O.D. was not found even when the human IgG agglutinating through heating (HAG-IgG) to be captured by the Clq was added at a concentration of 40 µg/mL or IFX or adalimumab was added at a concentration of 40 µg/mL.

Accordingly, it was found that the amount of ATA in an analyte can be specifically calculated from the optical density of the analyte on the basis of the dose-response curve (calibration curve).

Example 6: Measurement of Antibodies to Adalimumab (ATA) in Plasma from Patient <2>

1. Preparation of Samples

To 120 µL of plasma collected from patients (five cases) with inflammatory bowel disease who had experienced the occurrence of LOR to adalimumab (ADA) maintenance therapy, 360 µL of the diluent was added to dilute by 4-fold, and the diluted plasma was dispensed in an amount of 200 µL into each of two microtubes, and 50 µL of adalimumab (125 µg/mL) prepared with the diluent or 50 µL of the diluent was added thereto to be mixed together, and the resultant was then reacted at 4° C. overnight (final dilution rate: 5-fold).

2. Immunoassay

The samples prepared in the above 1 were dispensed in an amount of 100 µL into each well of a Clq-coated plate prepared in the same manner as in Example 5, and reacted in accordance with the method illustrated in 3. Immunoassay in Example 5 and then the amount of ATA in the samples was determined on the basis of the calibration curve shown in FIG. 6.

3. Results

For the plasma from five patients who developed LOR to adalimumab (ADA), addition of ADA further promoted formation of ADA-ATA immune complexes to result in measurement values significantly higher than those for no addition of ADA (P=0.0063) (FIG. 7).

From these results, it was found that the method based on addition of adalimumab according to the present invention allows measurement of the amounts or amount of ATA binding to ADA and/or ATA not binding to ADA contained in the plasma of a patient.

Example 7: Influence of Addition of Calcium (Ca) in ADAs-Clq ELISA 7-1. Influence of Addition of Calcium in ADAs-Clq ELISA Measurement System <Preparation of Reagents>
1) PBS (phosphate buffered saline);
PBS(−): NaCl 137 mmol/L, KCl 2.68 mmol/L, $KHPO_4$ 2 mmol/L, $NaH_2PO_4.12H_2O$ 10 mmol/L, pH 7.4
2) Blocking Buffer;
To PBS(−),0.5% boiled (for 5 minutes) casein (Cat. No. C7078, Sigma-Aldrich Co., LLC.), 1% Tween® 20 (polysorbate 20), and 0.01% thimerosal were added.
3) Diluent;
Prepared by adding 0.1% BSA and 0.01% thimerosal to PBS(−).
4) Diluents with $CaCl_2$;
Prepared by adding $CaCl_2$ to the diluent so as to reach 0.3 mM, 0.6 mM, or 0.9 mM.

1. Preparation of Clq-Coated Plate (1) Clq (Cat. No. 01740, Sigma-Aldrich Co., LLC.) adjusted to have a concentration of 10 µg/mL with PBS(−) was dispensed in an amount of 100 µL into each well of a 96-well ELISA plate (MaxisorpF8 x12, Cat. No. 468667, Nunc), and the plate was left to stand at 4° C. overnight. The resultant plate was used as an ELISA plate for measuring ATI and ATA. For comparative measurement of an immune complex by using a Clq-coated plate prepared in accordance with a method by Hey et al. (Non Patent Literature 5), a 96-well ELISA plate was similarly coated with 5 µg/mL of Clq.

(2) The Clq solutions in the plate were discarded, and each well was washed once with 300 µL of PBS(−) containing 0.5% Tween® 20 (polysorbate 20).

(3) After washing, 300 µL of the blocking buffer was added, and reacted at room temperature for 1 hour. After the reaction, the solutions were discarded, and the plate was dried in air flow for 2 hours, and thus a Clq-coated plate was prepared.

2. Preparation of Samples (1) Preparation of Reference Samples

Anti-human IgG antibodies were used as a substitute for antibodies to IFX (ATI) reference samples.

To 50 µL of rabbit anti-human IgG (H+L) antibodies (Cat. No. ab7155, Abcam plc.), 100 µL of IFX (1 mg/mL) was added, and 850 µL of PBS(−) was further added thereto to reach 1 mL, and the resultant was reacted at 4° C. overnight.

After the reaction, 5 µL aliquots thereof were taken, and the diluents each in a volume of 995 µL with $CaCl_2$ at different concentrations were added to the aliquots for 200-fold dilution, and thus an ATI concentration of 500 ng/mL was achieved.

(2) Preparation of Heat Aggregated Human IgG (HAG-IgG) Solutions

Human IgG (I4506, Sigma-Aldrich Co., LLC.) at a concentration of 4 mg/mL was heated at 63° C. for 20 minutes, and centrifuged at 10,000×g for 5 minutes, and the supernatant was then collected, and thus HAG-IgG was prepared. Therefrom, 10 μL of the HAG-IgG was taken, and 990 μL of PBS(−) was added thereto, and thus a concentration of 40 μg/mL was achieved. 5 μL aliquots thereof were taken, and the diluents each in a volume of 995 μL with $CaCl_2$ at different concentrations added were added to the aliquots for 200-fold dilution, and thus 200 ng/mL of HAG-IgG was prepared.

3. Immunoassay (A) Immune Complexes (ICs) ELISA by Using Coated C1q Method and Ca Concentration (1) The HAG-IgG solution (200 ng/mL) prepared in the above 2(2) was dispensed in an amount of 100 μL into each well of the C1q-coated plate, and reacted at 25° C. for 1 hour with stirring by using a plate mixer.

(2) Subsequently, the reaction solutions were discarded, and a procedure in which 300 μL of PBS(−) containing 0.5% Tween® 20 (polysorbate 20) (Cat. No. 1706531, Bio-Rad Laboratories, Inc.) was added to each well, and the solution was then discarded, was repeated four times to wash each well.

(3) HRP-labeled goat anti-human IgG antibody (ab81202, Abcam plc.) was diluted by 16,000-fold with a solution prepared by adding 0.5% casein to 0.5% Tween® 20 (polysorbate 20)-containing PBS(−), and the resultant was dispensed in an amount of 100 μL into each well, and reacted at 25° C. for 1 hour with stirring by using a plate mixer.

(4) After the reaction, the solutions were discarded, and a procedure in which 300 μL of 0.5% Tween® 20 (polysorbate 20)-containing PBS(−) was added to each well, and the solution was then discarded, was repeated four times to wash each well.

(5) A TMB Blue substrate solution (Cat. No. S1601, Dako) in a volume of 100 μL was added to each well, and the resultant was stirred, and then left to stand at room temperature under shaded conditions for 30 minutes.

(6) After development of color, 50 μL of $1N$-$H_2SO_4$ was added to each well to terminate the reaction, and the optical density was measured at wavelengths of 450 nm/650 nm by using a plate reader (absorptiometer for 96-well plates).

(B) ATI-C1q ELISA and Ca Concentration (1) The ATI reference material (500 ng/mL) prepared in the above 2(1) was dispensed in an amount of 100 μL into each well of the C1q-coated plate, and reacted at 25° C. for 2 hours with stirring by using a plate mixer.

(2) Subsequently, the reaction solutions were discarded, and a procedure in which 300 μL of PBS(−) containing 0.5% Tween® 20 (polysorbate 20) (Cat. No. 1706531, Bio-Rad Laboratories, Inc.) was added to each well, and the solution was then discarded, was repeated four times to wash each well.

(3) HRP-labeled human anti-infliximab monoclonal antibody (Cat. No. HCA216P, Bio-Rad AbD Serotec, Ltd.) was diluted by 1,000-fold with Can Get Signal Solution 2 (Cat. No. NKB-301, TOYOBO CO., LTD.), and the resultant was dispensed in an amount of 100 μL into each well, and reacted at 25° C. for 1 hour with stirring by using a plate mixer.

(4) After the reaction, the solutions were discarded, and a procedure in which 300 μL of 0.5% Tween® 20 (polysorbate 20)-containing PBS(−) was added to each well, and the solution was then discarded, was repeated four times to wash each well.

(5) A TMB Blue substrate solution (Cat. No. S1601, Dako) in a volume of 100 μL was added to each well, and the resultant was stirred, and then left to stand at room temperature under shaded conditions for 30 minutes.

(6) After development of color, 50 μL of $1N$-$H_2SO_4$ was added to each well to terminate the reaction, and the optical density was measured at wavelengths of 450 nm/650 nm by using a plate reader (absorptiometer for 96-well plates).

4. Results

Even in the case that $CaCl_2$ was added to 200 ng/mL of HAG-IgG in measurement, the increase of the optical density was not quite clear (FIG. 8-A). In the case that $CaCl_2$ was added to the ATI-C1q ELISA measurement system with the reference sample having a concentration of 500 ng/mL, in contrast, the optical density increased in a concentration-dependent manner, and reached to a plateau at a concentration of 0.6 mM (FIG. 8-B). Accordingly, addition of $CaCl_2$ to an ATI-C1q ELISA measurement system is expected to impart higher sensitivity and stability to the measurement system.

7-2. Influence of Addition of Ca on ADAs-C1q ELISA Dose-Response Curve

<1> ATI-C1q ELISA Dose-Response Curve and Addition of Ca

1. Preparation of Samples

Preparation of Reference Samples

To 10 μL of rabbit anti-human IgG (H+L) antibodies (2 mg/mL, Cat. No. ab7155, Abcam plc.), 20 μL of IFX (1 mg/mL) was added, and 470 μL of the diluent or the diluent with 0.6 mM $CaCl_2$ was further added thereto, and the solutions of two types of diluents were reacted at 4° C. overnight.

After the reaction, 500 μL of each diluent was added to achieve a concentration of 20 μg/mL, and 100 μL was taken therefrom, and 900 μL of each diluent was added thereto to achieve a concentration of 2 μg/mL. 500 μL thereof was taken and serially diluted with each diluent to prepare reference materials having concentrations of 31.25 ng/mL, 62.5 ng/mL, 125 ng/mL, 250 ng/mL, 500 ng/mL, 1,000 ng/mL, and 2,000 ng/mL, respectively.

2. Immunoassay

The samples prepared in the above 1 were dispensed in an amount of 100 μL into each well of a C1q-coated plate prepared in the same manner as in 1. Preparation of C1q-coated plate of "7-1" described above, and reacted in accordance with the method illustrated in 3. Immunoassay in Example 7, and then the optical density of the reference samples was measured.

3. Results

Addition of 0.6 mM $CaCl_2$ to the diluent of the measurement system provided optical densities in the dose-response curve 1.5 to 4 times higher than those for no addition of 0.6 mM $CaCl_2$, and thus increased sensitivity was provided (FIG. 8-C).

<2> ATA-C1q ELISA Dose-Response Curve and Addition of Ca

1. Preparation of Samples

Preparation of Reference Samples

Anti-human IgG antibodies were used as a substitute for antibodies to adalimumab (ATA) reference samples.

To 10 μL of rabbit anti-human IgG (H+L) antibodies (2 mg/mL, Cat. No. ab7155, Abcam plc.), 20 μL of adalimumab (1 mg/mL) was added, and 470 μL of the diluent or the diluent with 0.6 mM CaCl₂ was further added thereto, and the solutions of two types of diluents were reacted at 4° C. overnight.

After the reaction, 500 µL of each diluent was added to achieve a concentration of 20 µg/mL, and 10 µL was taken therefrom, and 990 µL of each diluent was added thereto to achieve a concentration of 200 ng/mL. 500 µL thereof was taken and serially diluted with each diluent to prepare reference materials having concentrations of 1.56 ng/mL, 3.125 ng/mL, 6.25 ng/mL, 12.5 ng/mL, 25 ng/mL, 50 ng/mL, and 100 ng/mL, respectively.

2. Immunoassay

The samples prepared in the above 1 were dispensed in an amount of 100 µL into each well of a C1q-coated plate prepared in the same manner as in 1. Preparation of C1q-coated plate of "7-1" described above, and reacted in accordance with the method illustrated in 3. Immunoassay in Example 5, and then the optical density of the reference samples was measured.

3. Results

Addition of 0.6 mM CaCl₂ to the diluent of the measurement system provided optical densities 2 to 4 times higher than those for no addition of 0.6 mM CaCl₂, and thus increased sensitivity was provided (FIG. 8-D).

The invention claimed is:

1. A method for detecting anti-drug antibodies (ADAs) to a drug in an analyte, the method comprising:
    (1) providing a sample comprising an analyte to be measured for ADAs by adding the drug to the analyte to be measured for ADAs to yield a sample comprising drug-ADAs immune complexes;
    (2) after (1), contacting the sample with a carrier coated with complement C1q, anti-C3d antibody, or anti-C1q antibody to capture the drug-ADAs immune complexes;
    (3) after (2), washing the coated carrier to exclude free-form drug;
    (4) after (3), contacting a labeled or non-labeled antibody specific to the drug with the drug-ADAs immune complexes captured with the coated carrier;
    (5) after (4), washing the coated carrier to exclude unbound labeled or non-labeled antibody specific to the drug; and
    (6) after (5) detecting the drug-ADAs immune complexes binding to the complement C1q, anti-C3d antibody, or anti-C1q antibody with the labeled or non-labeled antibody specific to the drug by at least one immunoassay selected from the group consisting of enzyme immunoassay, chemiluminescence method, immunochromatography, plasmon resonance, fluorescence method, radioimmunoassay, immunoradiometric assay, fluorescence polarization immunoassay, immunonephelometry, latex agglutination turbidimetru, latex agglutination inhibition immunoassay, and time-resolved fluorescence immunoassay.

2. The method according to claim 1, wherein the drug added in (1) is in an amount sufficient to recover ADAs present in the analyte.

3. The method according to claim 1, wherein the drug is an anti-TNFα drug.

4. The method according to claim 3, wherein the drug is infliximab, adalimumab, golimumab, or certolizumab pegol.

5. The method according to claim 3, wherein the drug is infliximab or adalimumab.

6. The method according to claim 1, wherein the antibody in 4 is a labeled antibody.

7. The method according to claim 6, wherein the labeled antibody is an enzyme-labeled antibody.

8. The method according to claim 1, wherein the analyte to be measured is an analyte collected from a patient given the drug.

9. The method according to claim 1, wherein the contacting a labeled or non-labeled antibody to the drug with the coated carrier comprises contacting in the presence of calcium ion.

* * * * *